United States Patent [19]

Bellamy et al.

[11] 4,360,435
[45] Nov. 23, 1982

[54] PROCESS FOR STERILIZING AND TRANSFERRING A SOLUTION

[75] Inventors: David Bellamy, Kenilworth; John L. Quick, Buffalo Grove, both of Ill.

[73] Assignee: Baxter Travenol Laboratories, Inc., Deerfield, Ill.

[21] Appl. No.: 90,235

[22] Filed: Nov. 1, 1979

[51] Int. Cl.³ .............................................. B01D 13/00
[52] U.S. Cl. ................................. 210/636; 128/272.3; 210/927; 422/1
[58] Field of Search ............ 210/500 M, 257 M, 23 F, 210/23 H, 94, 927, 636; 128/272.3, 214 F, 272; 73/38, 45.5, 40.7; 55/270; 422/1

[56] References Cited

U.S. PATENT DOCUMENTS

| | | | |
|---|---|---|---|
| 1,135,658 | 4/1915 | Bartlett | 210/446 |
| 1,205,743 | 11/1916 | Hoke | 210/927 |
| 2,879,207 | 3/1959 | Poitras | 195/139 |
| 2,901,112 | 8/1959 | Naftulin et al. | 210/94 |
| 2,954,028 | 9/1960 | Smith | 128/214 |
| 3,197,285 | 7/1965 | Rosen | 23/253 |
| 3,199,511 | 8/1965 | Kulick | 128/214 |
| 3,217,711 | 11/1965 | Pecina et al. | 128/214 |
| 3,298,597 | 1/1967 | Bellamy, Jr. | 229/59 |
| 3,595,231 | 7/1971 | Pistor | 128/215 |
| 3,635,798 | 1/1972 | Kirkham et al. | 195/103.5 |
| 3,675,780 | 4/1972 | Marshall | 128/214 |
| 3,709,365 | 1/1973 | Czaplinski et al. | 210/446 X |
| 3,722,557 | 3/1973 | Huggins | 141/59 |
| 3,730,353 | 5/1973 | Trasen et al. | 210/445 |
| 3,941,126 | 3/1976 | Dietrich et al. | 128/214 R |
| 3,986,506 | 10/1976 | Garber et al. | 128/272 X |
| 4,009,714 | 2/1977 | Hammer | 128/214 |
| 4,036,698 | 7/1977 | Bush | 128/214 |
| 4,073,691 | 2/1978 | Ahnell et al. | 195/103.5 M |
| 4,113,627 | 9/1978 | Leason | 210/446 |
| 4,116,646 | 9/1978 | Edwards | 210/DIG. 23 X |
| 4,177,149 | 12/1979 | Rosenberg | 210/500 M X |
| 4,223,675 | 9/1980 | Williams | 128/272 |
| 4,235,233 | 11/1980 | Mouwen | 128/272 X |
| 4,265,760 | 5/1981 | Abel et al. | 210/927 X |

FOREIGN PATENT DOCUMENTS 1543404  4/1979  United Kingdom ............ 210/321.1

Primary Examiner—Frank A. Spear, Jr.
Attorney, Agent, or Firm—John P. Kirby, Jr.; George H. Gerstman; Bradford R. L. Price

[57] ABSTRACT

A process for sterilizing a solution and thereafter transferring it to a solution container for storage. A sterilizing filter, flexible tubing and the solution container are provided as a pre-sterilized unit with a label indicating that the unit is sterile. A source of solution to be transferred is connected to an inlet of the sterilizing filter, and the solution is sterilized by transferring it from the source and through the sterilizing filter to the container via the flexible tubing. The integrity of the filter is determined by introducing a pressurized gas into the filter and observing through a light-transmissive portion in the sterile unit for gas bubbles, which would indicate a loss of filter integrity and unit sterility.

6 Claims, 1 Drawing Figure

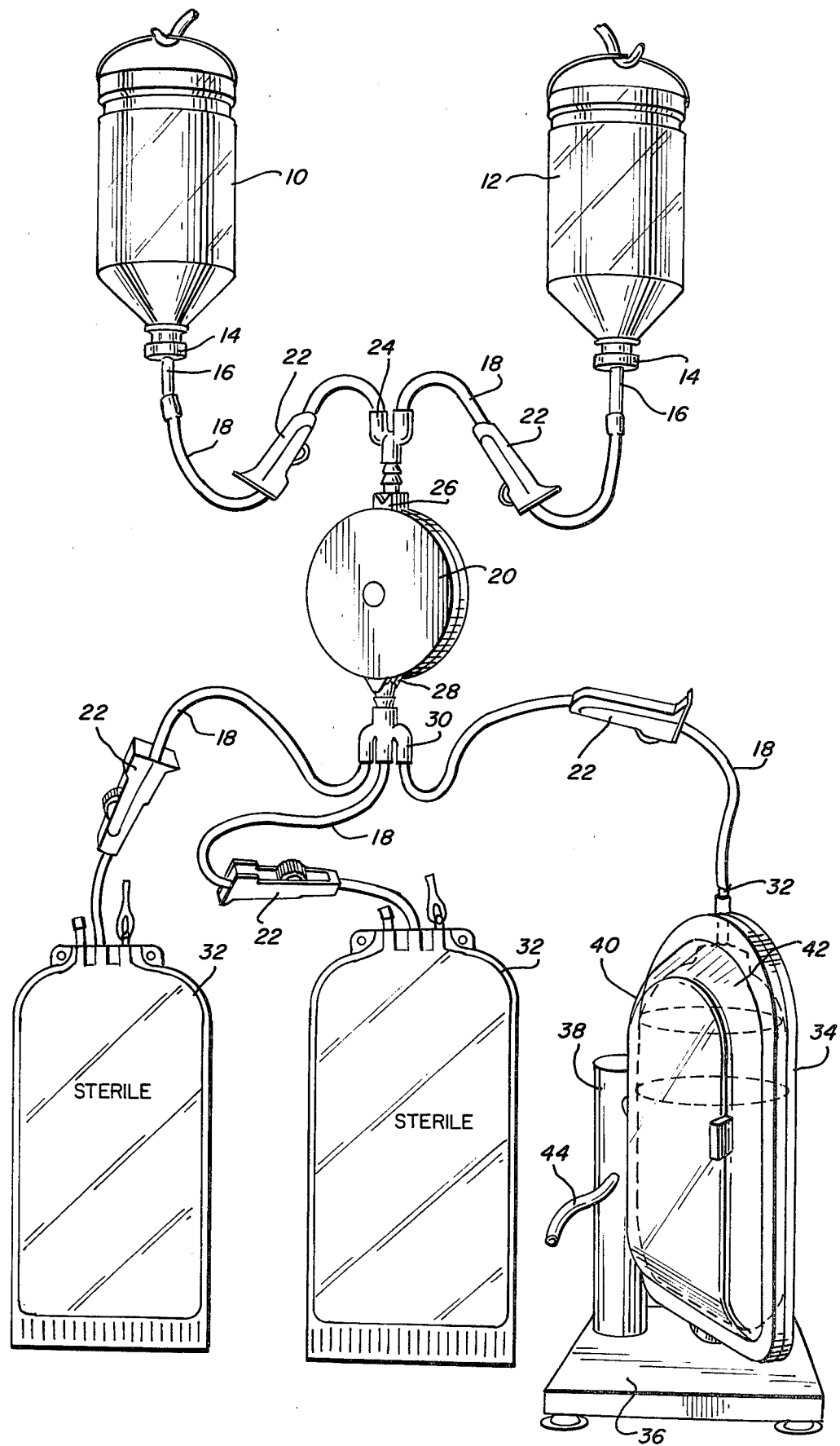

PROCESS FOR STERILIZING AND TRANSFERRING A SOLUTION

BACKGROUND OF THE INVENTION

The present invention pertains to a process and apparatus for the transfer and sterilization of a solution. More particularly, it pertains to such a process and apparatus useful for the compounding of hyperalimentation solutions.

Hyperalimentation therapy is the intravenous feeding of, for example, a protein-carbohydrate mixture to a patient. It is used primarily to meet his protein and caloric requirements which are unable to be satisfied by oral feeding.

The protein may be in the form of free-amino acids or protein hydrolysate and the carbohydrate commonly used is dextrose. In addition to the protein and carbohydrate, vitamins (water-soluble and fat-soluble) and electrolytes can also be supplied in this therapy.

Each of these parenteral ingredients and the combination thereof are particularly susceptible to the growth of deleterious organisms and it is desirable that they be administered to the patient in a sterile condition. Thus, because these protein and carbohydrate solutions cannot be precompounded by the manufacturer, but must be combined at the time of their use, their compounding must be performed under sterile conditions to avoid organism growth.

A known apparatus and process for compounding hyperalimentation solutions utilizes a solution transfer system including a plastic receiving container and a Y-transfer set. A plastic container found to be particularly useful is one manufactured by Travenol Laboratories, Inc., of Deerfield, Illinois and marketed under the trademark VIAFLEX®. A known Y-transfer set includes two separate tubes, each having an end attached to a common juncture by which solutions delivered through the tubes will pass through the juncture into the attached plastic container. The other end of one tube of the set is attached to a protein holding container and of the other tube of the set to a carbohydrate holding container. The desired volume of each solution being transferred to the receiving container is controlled by a roller clamp placed on each tube. Each solution may be allowed to flow into the plastic container by gravity flow. However, it has been found to be useful to transfer same under the influence of a vacuum applied to the receiving container, which vacuum is created in a vacuum chamber into which the container is placed, such as the one manufactured by Travenol Laboratories, Inc., of Deerfield, Ill. and marketed under the trademark VIAVAC®.

It has been known in the past that to maintain sterility during the compounding of hyperalimentation solutions, compounding should be perform under a laminar flow hood. Laminar flow hoods are useful for reducing the risk of airborne contamination of such solutions. These units operate by taking room air and passing it through a prefilter to remove gross contaminants, such as dust and lint. The air is then compressed and channeled through a bacterial retentive filter in the hood in a laminar flow fashion. The purified air flows out over the entire work surface of the hood in parallel lines at a uniform velocity. This type of filter is designed to remove essentially all bacteria from the air being filtered.

Compounding under a laminar flow hood aids in preventing airborne contamination, but it is relatively cumbersome and expensive. When using such a hood the operator might inadvertently perform the work at the edge or outside of the hood and not at least 6 inches within the hood to insure the benefits of the air being purified. Time must be taken and care must be exercised to maintain a direct open path between the filter and the compounding area. Solution bottles and other non-sterile objects cannot be placed at the back of the hood work area next to the filter because these objects could contaminate everything downstream and disrupt the laminar flow pattern of the purified air. Also, in using a laminar flow hook, it is necessary to routinely clean the work surface of the hood before any compounding is performed.

Therefore, it is the object of the present invention to provide a process and apparatus for transferring a solution from a holding container to a receiving container, such as a receiving bag of the type above identified, while also sterilizing such solution.

Another important object of the present invention is to provide a readily available process and apparatus for transferring and sterilizing the solution being transferred without the necessity of a laminar flow hood.

Other objects and advantages of present inventions will become apparent from the description of this invention that follows.

SUMMARY OF THE INVENTION

In accordance with the present invention, an apparatus is provided for transferring at least one solution into at least one solution receiving container and for also sterilizing the solution during the transfer process. The apparatus includes a solution receiving container; a filter capable of sterilizing the solution, the filter having means by which the solution can be directed into the sterilizing portion of the filter and an outlet; and tubing connected between the filter outlet and the container for transfer of the sterilized solution from the filter into the container. At least the sterilizing portion of the filter, the filter outlet, the tubing, and the container are combined and labeled for use as a sterile unit.

In one embodiment of the invention means are provided for determining whether the integrity of the filter, and consequently the sterility of the unit, has been maintained during the transfer process. Such means preferably include an inlet into the filter by which a pressurized gas may be introduced and a transparent portion in the sterile unit through which the presence of gas bubbles can be determined, which would indicate a loss of filter integrity and unit sterility.

In another embodiment of the invention, the apparatus includes a vacuum source operable on the container to create a pressure differential between the inside and outside of the container, thereby facilitating solution transfer to the container.

The process of this invention includes the steps of delivering the solution from a solution source to the sterile unit, sterilizing the solution by transferring it through the filter, and transferring the sterilized solution through the filter outlet and tubing into the container. In one embodiment of this invention, the above mentioned pressure differential is created by the operation of a vacuum chamber into which the container has been placed. Upon the successful completion of the transfer and sterilizing operation, the container is hermetically sealed by the application of external compression to the tubing, heat sealing of the tubing, or heat sealing of the container at a point adjacent the connection of the tubing to the container.

A more detailed explanation of the invention is provided in the following description and claims, for which reference to the accompanying drawing should be made.

BRIEF DESCRIPTION OF THE DRAWING

FIG. 1 is a perspective view of a preferred embodiment of the apparatus of the present invention.

DETAILED DESCRIPTION OF THE PREFERRED EMBODIMENT

An apparatus of the present invention for compounding hyperalimentation solutions generally includes a filter, a plastic, extensible, parenteral solution bag, and tubing connecting the outlet of the filter to the bag. Once these elements are connected, the combination is sterilized and made available as a sterile unit, which unit is labeled for sale as being sterile.

Briefly, in the transfer operation, the solutions to be transferred are selected and a vacuum chamber is made available. The filter of the sterile unit is connected to the containers holding the solutions and the bag to be filled is placed in the vacuum chamber. The solutions, prior to their transfer, may or may not be sterile. However, once they are transferred through the sterilizing filter into the bag, there is no need for resterilization of the resultant, sterilized solution. The solutions are transferred through the filter and into the bag under the influence of a vacuum created in the vacuum chamber, which accelerates the transfer process. The bag is then sealed. However, it has been found to be advantageous to verify the integrity of the sterile unit, and the sterility of the transferred solution, prior to the bag being sealed. This is accomplished by the introduction into the filter of either air or another gas to ascertain if such gas passes through the filter, which is indicated by the presence of bubbles in a transparent portion of the sterile unit. If such bubbles are present, because sterility of the transferred solution has not been achieved, the solution would be discarded. The following is a more detailed description of the structural elements shown in FIG. 1.

Referring to FIG. 1, there is shown a first solution container 10 and a second solution container 12. Generally these solution containers are made of glass and have means by which they may be connected to tubing for transfer or administration purposes. As shown in FIG. 1, the containers each have a stopper 14 into which a spike 16 is inserted. Each spike is attached to one end of a tubing 18 by which the solution in each of these solution holding containers can be transferred to a filter 20. A roller clamp 22 is provided for controlling the flow of solution through each tubing 18. The other end of each tubing is inserted into a Y-connector 24 which is attached to an inlet 26 of filter 20. Herein, inlet encompasses any means by which the solution to be transferred is presented to and may pass through the filter, such as an opening in the filter by which the solution is presented to the filtering and sterilizing media of the filter.

Filter 20 is a sterilizing filter by which the solution passing through the filter is made essentially bacteria free prior to its further transfer. Preferably, the filter is a hydrophilic, bacterial organism retentive filter having a membrane surface area that is greater than one centimeter and a maximum pore size of about 0.22 microns. Filters found to be particularly useful in the present invention are manufactured by the Millipore Corporation of Bedford, Mass. under the trademark MILLIPORE.

Proceeding downward in FIG. 1 from filter 20, the filter has an outlet 28 to which is attached a triple-branch, connector 30. Tubing similar to tubing 18 described above is inserted into each branch of connector 30. Again, a roller clamp 22 is utilized on each tubing 18 to control the flow therethrough. The other end of each tubing 18 is attached to a flexible, plastic bag 32 in a manner well known in the art. As shown in FIG. 1, bag 32 is placed in a vacuum chamber 34 to be filled in the manner discussed below. A vacuum chamber found to be particularly useful in accordance with the present invention is disclosed in U.S. Pat. No. 3,722,557, the disclosure which is incorporated by reference herein. Such a vacuum chamber includes a base 36, a support post 38, and top and bottom members, 40 and 42, which are hinged together. The vacuum drawn in the chamber is sourced through a vacuum hose 44.

The solutions contained in holding containers 10 and 12 are generally sterilized during their manufacture and packaging. However, to transfer these solutions to another container or administer them, the holding containers must be open to the environment so air can enter therein for affecting solution flow. Once this occurs the possibility of contamination exists. Further, in handling spikes 16 and the other apparatus connected to containers 10 and 12, touch contamination is also possible. Therefore, whatever the condition of sterility of the solutions, filter 20 sterilizes the final solution being transferred into bag 32.

In the transfer operation, filter 20, bags 32, the tubing 18 connecting the filter and bags, and the roller clamps 22 associated therewith are combined and presented for use as a sterile unit. Solution holding containers 10 and 12 and the elements associated therewith are connected to inlet 26 of filter 20. The first bag 32 to be filled is placed in vacuum chamber 34. The actual operation of the various clamps and vacuum chamber by which the solutions are transferred into the bag is well known and need not be further discussed. Of course, it should be understood that the bags can be filled in sequential order or all at one time by the use of multiple vacuum chambers.

Once the bag is filled, it has been found to be advantageous to check the integrity of filter 20 and determine whether any leaks or other conditions have arisen during the transfer process by which the sterility of the transferred solution may have been compromised. Preferably, with the aid of the application of a vacuum on the filled bag, air or another gas is introduced into filter 20. By directing such a gas into inlet 26 (after the tubing 18 associated with holding containers 10 and 12 has been disconnected therefrom) or another opening in filter 20, the operator can determine from gas bubbles in a transparent portion of the sterile unit whether the integrity of the filter, and consequently the sterility of the transferred solution, has been maintained. Of course, if a vacuum chamber is not used in the operation the gas can be pressurized instead. If no such bubbles appear in the solution being sterilized, bag 32 is hermetically sealed by either external compression of tubing 18 connected thereto, heat sealing of this tubing, or heat sealing of the bag itself adjacent a point where the tubing connects to the bag.

Although only preferred embodiments of the present invention have been shown in FIG. 1 and described with respect thereto, various modifications to and other improvements in this invention will be apparent to one skilled in the art.

What is claimed is:

1. A process for sterilizing a solution and thereafter transferring it to a solution container for storage, which comprises the steps of:

providing at least one solution container having an inlet;

providing a sterilizing filter capable of sterilizing a solution and having a maximum pore size of about 0.22 micron, said filter having an outlet;

providing flexible tubing connected to the inlet of said solution container and to the outlet of the sterilizing filter, to provide a fluid path between the filter and the solution container;

providing said sterilizing filter, flexible tubing and container as a pre-sterilized unit with a label indicating that said unit is sterile;

connecting a source of solution to be transferred to an inlet of said sterilizing filter;

sterilizing the solution by transferring it from the source, through the sterilizing filter and to the container via said flexible tubing;

determining whether the integrity of the filter, and consequently the sterility of the unit, has been maintained during the transfer process, said determining step comprising the steps of introducing a pressurized gas into the filter and observing through a light-transmissive portion in the sterile unit for gas bubbles, which would indicate a loss of filter integrity and unit sterility.

2. The process of claim 1 wherein the container is flexible and further comprising the step of creating a pressure differential between the inside and outside of the container to facilitate solution transfer from the filter into the container.

3. The process of claim 1 wherein the gas is directed into the filter in the same manner as is the solution being transferred.

4. The process of claim 1 wherein the gas is directed through a reclosable opening in the filter.

5. The process of claim 1 wherein the container is hermetically sealed by the sealing of the tubing.

6. The process of claim 1 wherein the container is hermetically sealed by being sealed at a point adjacent the connection of the tubing to the container.

* * * * *